US012667735B2

(12) United States Patent
Maytin

(10) Patent No.: US 12,667,735 B2
(45) Date of Patent: Jun. 30, 2026

(54) METHODS FOR REDUCING PAIN DURING PHOTODYNAMIC THERAPY OF ACTINIC KERATOSIS

(71) Applicant: Sun Pharmaceutical Industries, Inc., Princeton, NJ (US)

(72) Inventor: Edward V. Maytin, Cleveland, OH (US)

(73) Assignee: Sun Pharmaceutical Industries, Inc., Princeton, NJ (US)

( * ) Notice: Subject to any disclaimer, the term of this patent is extended or adjusted under 35 U.S.C. 154(b) by 1074 days.

(21) Appl. No.: 17/621,317

(22) PCT Filed: Jun. 23, 2020

(86) PCT No.: PCT/IB2020/055937
§ 371 (c)(1),
(2) Date: Dec. 21, 2021

(87) PCT Pub. No.: WO2020/261125
PCT Pub. Date: Dec. 30, 2020

(65) Prior Publication Data
US 2022/0362573 A1      Nov. 17, 2022

Related U.S. Application Data

(60) Provisional application No. 62/866,311, filed on Jun. 25, 2019.

(51) Int. Cl.
| | |
|---|---|
| *A61N 5/06* | (2006.01) |
| *A61K 41/00* | (2020.01) |
| *A61P 29/00* | (2006.01) |

(52) U.S. Cl.
CPC .......... *A61N 5/062* (2013.01); *A61K 41/0061* (2013.01); *A61P 29/00* (2018.01); *A61N 2005/0663* (2013.01)

(58) Field of Classification Search
CPC ............ A61N 5/062; A61N 2005/0663; A61N 2005/0626; A61N 2005/0662;
(Continued)

(56) References Cited

U.S. PATENT DOCUMENTS

| | | | |
|---|---|---|---|
| 2010/0137439 A1* | 6/2010 | Wulf ................... | A61K 31/221 |
| | | | 514/561 |
| 2010/0174223 A1 | 7/2010 | Sakamoto et al. | |

(Continued)

FOREIGN PATENT DOCUMENTS

| | | |
|---|---|---|
| JP | 2005-520606 A | 7/2005 |
| JP | 2010-515714 A | 5/2010 |

(Continued)

OTHER PUBLICATIONS

Gandy, J. et al., "Photodynamic Therapy Effectively Treats Actinic Keratoses Without Pre-Illumination Incubation Time"; J. Drugs Dermatol 16(3); Mar. 2017; pp. 275-278.

(Continued)

*Primary Examiner* — William J Levicky
*Assistant Examiner* — Sebastian X Lukjan
(74) *Attorney, Agent, or Firm* — Foley & Lardner LLP

(57) ABSTRACT

This present invention and its embodiments relates to methods for reducing pain during photodynamic therapy of actinic keratosis. The present invention also relates to methods of treating actinic keratosis with reduced pain during photodynamic therapy of actinic keratosis.

15 Claims, 3 Drawing Sheets

Just before PDT 4 days after PDT

An example of AK lesions on the forehead, at baseline (prior to PDT) and at 4 days after PDT. Note that the extent of post-PDT erythema appears to be very similar on Sides A and B.

(58) Field of Classification Search
     CPC .............. A61N 5/0616; A61K 41/0061; A61K
                      31/197; A61P 29/00; A61P 17/00
     See application file for complete search history.

(56) References Cited

U.S. PATENT DOCUMENTS

| | | | |
|---|---|---|---|
| 2011/0082410 A1 | 4/2011 | Volker et al. | |
| 2014/0067024 A1* | 3/2014 | Jones ................... | A61N 5/0616 |
| | | | 607/90 |
| 2016/0030565 A1 | 2/2016 | Wulf et al. | |
| 2016/0367832 A1 | 12/2016 | Jones et al. | |

FOREIGN PATENT DOCUMENTS

| | | |
|---|---|---|
| JP | 2017-505292 A | 2/2017 |
| WO | WO-2008/052350 A1 | 5/2008 |
| WO | WO-2008/084241 A2 | 7/2008 |

OTHER PUBLICATIONS

Anand et al., Biomodulatory Approaches to Photodynamic Therapy for Solid Turmors, Cancer Letters, 326, 2012, pp. 8-16.
Ang et al., Photodynamic Therapy and Pain: A Systematic Review, Photodiagnosis and Photodynamic Therapy, vol. 19, Jul. 15, 2017, pp. 308-344.
Braathen et al., Guidelines on the Use of Photodynamic Therapy for Nonmelanoma Skin Cancer: An International Consensus, The American Academy of Dermatology, Inc. 2007, pp. 125-143.
Christensen et al., Guidelines for Practical Use of MAL-PDT in Non-Melanoma Skin Cancer, JEADV, 2010, 24, pp. 505-512.
Harald Breivik, Fifty Years on the Visual Analogue Scale (VAS) for Pain-Intensity is Still Good for Acute Pain. But Multidimensional Assessment is Needed for Chronic Pain, Scandinavian Journal of Pain, 2016, pp. 150-152.
Kennedy et al., Endogenous Protoporphyrin IX, A Clinically Useful Photosensitizer for Photodynamic Therapy, J. Photochem. Photobiol. B: Biol., 14, 1992, pp. 275-292.
Pariser et al., Randomized Vehicle-Controlled Study of Short Drug Incubation Aminolevulinic Acid Photodynamic Therapy for Actinic Keratoses of the Face or Scalp, American Society for Dermatologic Surgery, Inc., 2016, pp. 296-304.
Piacquadio et al., Photodynamic Therapy With Aminolevulinic Acid Topical Solution and Visible Blue Light in the Treatment of Multiple Actinic Keratoses of the Face and Scalp, Arch Dermatol, vol. 140, Jan. 2004, pp. 41-46.
Warren et al., Pain Associated with Aminolevulinic Acid-Photodynamic Therapy of Skin Disease, Journal American Academy of Dermatology, Dec. 2009, pp. 1033-1043.
Extended European Search Report in EP20831638.0 dated Jun. 1, 2023.

* cited by examiner

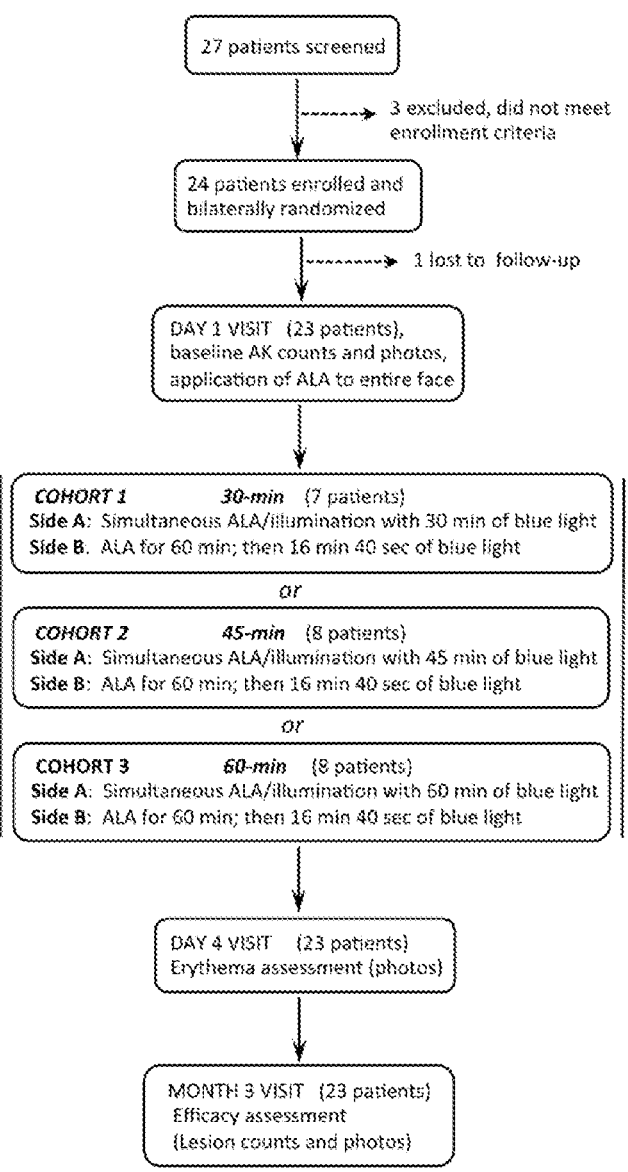
Fig. 1. Study design, and patient enrollment.

Just before PDT
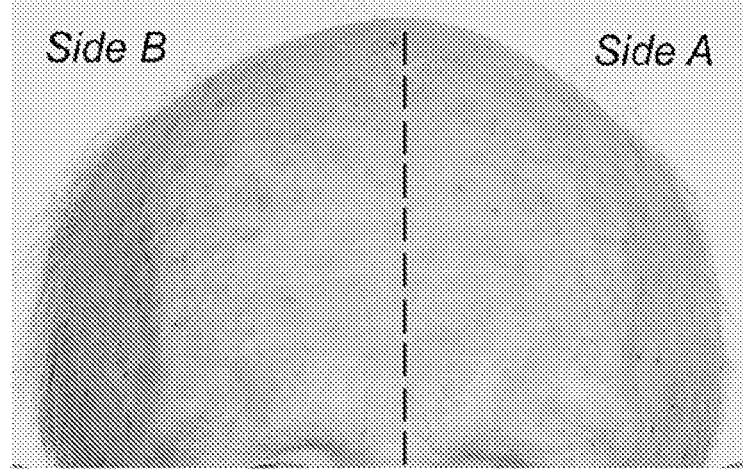
4 days after PDT
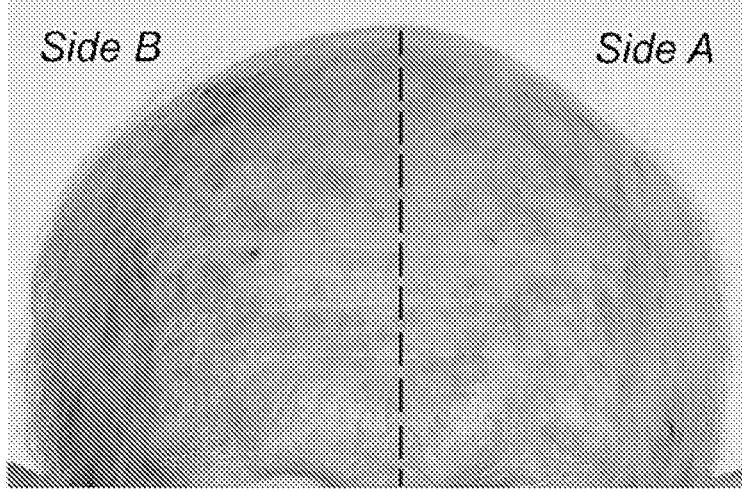
Fig 2. An example of AK lesions on the forehead, at baseline (prior to PDT) and at 4 days after PDT. Note that the extent of post-PDT erythema appears to be very similar on Sides A and B.

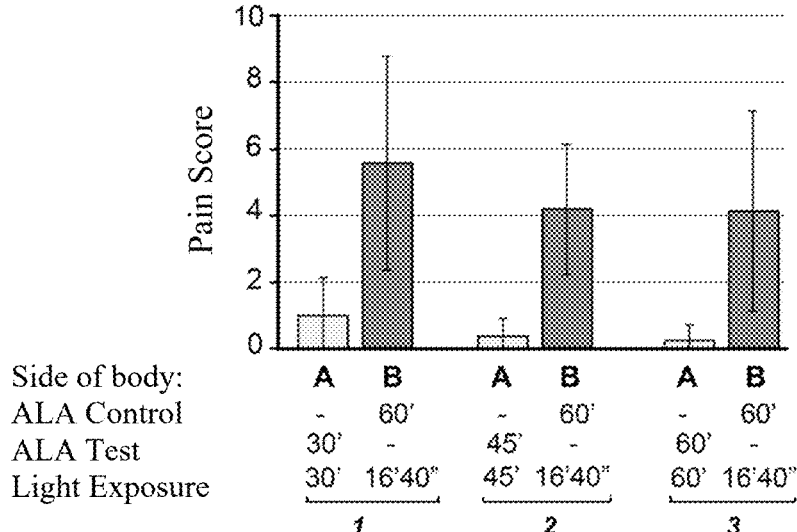
Fig. 3. Maximum pain scores reported by patients during PDT, on the side receiving Test PDT (Side A) and on the side receiving Control PDT (Side B). Bars represent mean ± SEM from patients in each of the three cohorts.

METHODS FOR REDUCING PAIN DURING PHOTODYNAMIC THERAPY OF ACTINIC KERATOSIS

FIELD OF THE DISCLOSURE

This present invention relates to methods for reducing pain during photodynamic therapy of actinic keratosis. The present invention also relates to methods of treating actinic keratosis with reduced pain during photodynamic therapy.

BACKGROUND

Photodynamic therapy (PDT), photodynamic diagnosis (PD), or photochemotherapy is generally used to treat and/or diagnose several types of ailments in or near the skin or other tissues, such as those in a body cavity. For example, photodynamic therapy or photodynamic diagnosis may be used for treatment or diagnosis of actinic keratosis of the scalp or facial areas of a patient or the upper extremities (e.g., the dorsal surface of the hand or forearms). In addition, such techniques may be used for treatment and diagnosis of other indications (e.g., acne, warts, psoriasis, photo-damaged skin, cancer) and other areas of the patient (e.g., the legs or portions of the arms other than the forearms).

PDT is a field treatment that employs a photosensitizing drug and visible light to treat skin cancers and pre-cancers. PDT is FDA-approved for actinic keratoses (AK) in the U.S. (Piacquadio D J et al. *Arch Dermatol* 2004; 140:41-6.), and in Europe for basal cell carcinoma and squamous cell carcinoma as well (Christensen E et al. *J Eur Acad Dermatol Venereol* 2010; 24:505-12). PDT is performed by applying topical 5-aminolevulinic acid (ALA) or its methyl ester (m-ALA) to the lesional skin; these prodrugs are then selectively taken up by neoplastic cells and converted into protoporphyrin IX (PpIX) within mitochondria (Kennedy J C et al. *J Photochem Photobiol B* 1992; 14:275-92). Exposure to visible light activates the PpIX, damaging the mitochondria and triggering cell death (Anand S et al. *Cancer Lett* 2012; 326:8-16). PDT has important clinical advantages, including the ability to target large numbers of AK lesions simultaneously and to eliminate them without scarring (Piacquadio D J et al. *Arch Dermatol* 2004; 140:41-6; Christensen E et al. *J Eur Acad Dermatol Venereol* 2010; 24:505-12; Anand S et al. *Cancer Lett* 2012; 326:8-16). However, one downside of PDT is that patients often experience stinging pain during the illumination phase. PDT-induced pain, which occurs with either blue light or red light, is not alleviated by any topical anesthetic agent (other than ice chips and evaporative cooling), and can be so severe that patients refuse to complete the treatment and/or decline to undergo any future PDT (Warren C B et al. *J Am Acad Dermatol* 2009; 61:1033-43; Ang J M et al. *Photodiagnosis Photodyn Ther* 2017; 19:308-44). Therefore PDT-related pain represents a significant barrier to achieving optimal therapeutic outcomes.

Several lines of evidence suggest that PDT-associated pain is positively correlated with the length of time that ALA resides on the skin (ALA incubation time). Over the past two decades, practicing physicians have tried to gradually reduce the ALA incubation period. For example, a recent clinical trial of facial and scalp AK showed similar lesion clearance rates using ALA incubation times of 1, 2, or 3 hours (Pariser D M et al. *Dermatol Surg* 2016; 42:296-304). However, the FDA approved ALA photodynamic therapy is still associated with a 14-16 hours long and painful incubation time or a pre-illumination gap, perhaps because reduction of incubation time with an objective of pain management may severely hamper the therapeutic efficacy of the photodynamic therapy. Therefore, FDA has not yet approved a photodynamic therapy with minimum or substantially no pre-illumination gap. The inventors of the present invention have surprisingly found that a topical ALA application followed by exposure to blue light with substantially no pre-illumination gap, resulted not only in a very good efficacy for AK lesions but also resulted in almost no or minimal pain to the patients.

SUMMARY

Provided herein is a method of reducing pain during photodynamic therapy of actinic keratoses comprising: (a) applying a pharmaceutical composition comprising 5-aminolevulinic acid on the affected area of the skin of a patient; (b) illuminating the affected area with a light source with substantially no pre-illumination gap; and (c) maintaining the illumination for at least 30 minutes; wherein the method does not include a pre-treatment preparation.

Also provided herein is a method of treating actinic keratoses comprising: (a) applying a pharmaceutical composition comprising 5-aminolevulinic acid on the affected area of the skin of a patient; (b) illuminating the affected area with a light source with substantially no pre-illumination gap; and (c) maintaining the illumination for at least 30 minutes; wherein the method does not include a pre-treatment preparation.

BRIEF DESCRIPTIONS OF THE DRAWINGS

FIG. 1. Describes the study design, and patient enrollment.

FIG. 2. Provides an example of AK lesions on the forehead, at baseline (prior to PDT) and at 4 days after PDT. Note that the extent of post-PDT erythema appears to be very similar on Sides A and B.

FIG. 3. Describes the maximum pain scores reported by patients during PDT, on the side receiving Test PDT (Side A) and on the side receiving control PDT (Side B). Bars represent mean±SEM from patients in each of the three cohorts.

DETAILED DESCRIPTION

Various embodiments of the invention are described hereinafter.

The term "substantially no pre-illumination gap" is used to indicate the time difference or time gap between the application of topical composition of 5-aminolevulinic acid to the skin according to the invention and then illumination of the affected area of the skin with a light source. For the purpose of this invention, "substantially no pre-illumination gap" means a time gap not more than 10 min, preferably not more than 8 min, more preferably not more than 6 min, most preferably not more than 5 min.

The term "Visual Analogue Scale for Pain (referred to as VAS pain score hereafter) as used herein, is defined as follows: An 11-point numerical pain scale wherein patients report a number (from 0 to 10) that most closely reflects the level of pain they are experiencing at that particular moment; 0 corresponds to no pain and 10 corresponds to the worst pain imaginable (Breivik, *HaraldScandinavian Journal of Pain* 2016; 11:150-152).

The term "Pre-treatment preparation" as used herein includes, but is not limited to curettage, abrasive tape, micro-needling, laser surface preparation, scrubbing or descaling of the skin on and around lesion of actinic keratoses; or prior administration, including topical administration, of 5-fluorouracil, topical calcipotriol or any retinoid cream to the patient in need of such photodynamic therapy. Any procedures related to cleaning of the skin with an organic solvent such as isopropyl alcohol, ethyl alcohol, or acetone or other such suitable solvents or a mixture thereof, is not considered as a pre-treatment.

In one embodiment of the present invention, side A (the Test PDT) received topical application of composition of 5-aminolevulinic acid followed by continuous illumination, with substantially no pre-illumination gap, of the affected area of the skin, of a patient for at least 30 minutes, or at least 45 minutes, or at least 60 minutes.

In one embodiment of the present invention, side B (the Control PDT) received topical application of composition of 5-aminolevulinic acid; the composition was kept on the affected area for 1 hour followed by a standard illumination of the affected area of the skin of a patient for 16 minutes and 40 seconds.

The use of any and all examples, or exemplary language (e.g., "such as") provided herein, is intended merely to better illustrate the embodiments and does not pose a limitation on the scope of the claims unless otherwise stated.

In one aspect, the present invention relates to a method of reducing pain during photodynamic therapy of actinic keratoses comprising: (a) applying a pharmaceutical composition comprising 5-aminolevulinic acid on the affected area of the skin of a patient; (b) illuminating the affected area with a light source with substantially no pre-illumination gap; and (c) maintaining the illumination for at least 30 minutes; wherein the method does not include a pre-treatment preparation.

In one embodiment, the illumination is carried out for at least 45 minutes.

In another embodiment, the illumination is carried out for at least 60 minutes.

In one aspect of the invention the at least 30 minutes of illumination, the at least 45 minutes of illumination and/or the at least 60 minutes of illumination is achieved by using a single cycle of 30 minutes illumination, using one and a half cycle of 30 minutes illumination cycle or two cycles of 30 minutes illumination, respectively. An illumination cycle as used herein means that the light source is continuously kept in Switch On position for 30 minutes for illumination of the affected area of skin.

In one embodiment, the present invention relates to a method of reducing pain during photodynamic therapy of actinic keratoses wherein the pre-illumination gap is not more than 10 minutes. In a preferred embodiment, the pre-illumination gap is not more than 8 min. In a more preferred embodiment, the pre-illumination gap is not more than 6 min. In the most preferred embodiment, the pre-illumination gap is not more than 5 min.

In one embodiment, the present invention provides a method of reducing pain during photodynamic therapy of actinic keratoses comprising applying a pharmaceutical composition comprising 5-aminolevulinic acid on the affected area of the skin of a patient, wherein the therapeutically effective concentration of 5-aminolevulinic acid is 20% w/v.

In another embodiment, the present invention provides a method of reducing pain during photodynamic therapy of actinic keratoses comprising applying a pharmaceutical composition comprising 5-aminolevulinic acid on the affected area of the skin of a patient, wherein the therapeutically effective concentration of 5-aminolevulinic acid is 10% w/v.

In one embodiment, the present invention relates to a method of reducing pain during photodynamic therapy of actinic keratosis, wherein the affected area of the skin of a patient is illuminated with a light source after application of ALA. The light source may be selected from any physical light-generating device that generates blue, red, or white wavelengths, for example, the light source may be an arc lamp, an incandescent light (glowing filament), a fluorescent source (glowing gas), a laser (coherent light), a red light source, a halogen laser, a blue light source or a light emitting diode (LED).

In a preferred embodiment, the light source is a blue light source. In a more preferred embodiment, the light source is a blue light having a wavelength of approximately 417 nm and is applied at an intensity of 10 mW/cm$^2$ for 1000 seconds to provide a dose of 10 J/cm$^2$. In other embodiments, the intensity may be increased (for example, doubled) to reduce the treatment time. For example, the intensity may be increased to an extent wherein the treatment time becomes about one-half of the original treatment time. In another embodiment the intensity of the light may be decreased (for example, with neutral density filters) so as to increase the treatment time.

In another preferred embodiment, the light source is a red light source. In a more preferred embodiment, the red light source is a red light generated by light emitting diodes (LEDs) at, for example, 635 nm. The red light can provide a dose of, for example, 10 to 75 J/cm$^2$ (such as 37 J/cm$^2$), e.g., within 10 minutes. In other embodiments, the intensity may be increased (for example, doubled) to reduce the treatment time. For example, the intensity may be increased to an extent wherein the treatment time becomes about one-half of the original treatment time. In another embodiment the intensity of the light may be decreased (for example, with neutral density filters) so as to increase the treatment time.

In one embodiment of the invention, the VAS pain score achieved from the photodynamic therapy is less than 1.0. In preferred embodiments, the VAS pain score is selected from a value which is less than 0.9, less than 0.8, less than 0.7 or less than 0.6. In a more preferred embodiment, the VAS pain score is selected from a value which is less than 0.5, less than 0.4, less than 0.3, less than 0.2 or less than 0.1. In the most preferred embodiment, the VAS Pain Score is 0.0.

In another aspect, the present invention relates to a method of treating actinic keratoses comprising: (a) applying a pharmaceutical composition comprising 5-aminolevulinic acid on the affected area of the skin of a patient; (b) illuminating the affected area with a light source with substantially no pre-illumination gap; and (c) maintaining the illumination for at least one cycle of 30 minutes; wherein the method does not include a pre-treatment preparation.

In one embodiment, the illumination is carried out for at least 45 minutes.

In another embodiment, the illumination is carried out for at least 60 minutes.

In one embodiment, the at least 30 minutes of illumination, the at least 45 minutes of illumination or the at least 60 minutes of illumination is achieved by using a single cycle of 30 minutes illumination, using one and a half cycle of 30 minutes illumination cycle or two cycles of 30 minutes illumination, respectively. An illumination cycle as used herein means that the light source is continuously kept in Switch On position for 30 minutes for illumination of the affected area of skin.

In one embodiment, the present invention relates to a method of treating actinic keratoses using photodynamic therapy, wherein the pre-illumination gap is not more than 10 minutes. In a preferred embodiment, the pre-illumination gap is not more than 8 minutes. In a more preferred embodiment, the pre-illumination gap is not more than 6 minutes. In the most preferred embodiment, the pre-illumination gap is not more than 5 minutes.

In one embodiment, the present invention provides a method of treating actinic keratoses using photodynamic therapy comprising applying a pharmaceutical composition comprising 5-aminolevulinic acid on the affected area of the skin of a patient, wherein the therapeutically effective concentration of 5-aminolevulinic acid is 20% w/v.

In another embodiment, the present invention provides a method of treating actinic keratoses using photodynamic therapy comprising applying a pharmaceutical composition comprising 5-aminolevulinic acid on the affected area of the skin of a patient, wherein the therapeutically effective concentration of 5-aminolevulinic acid is 10% w/v.

In one embodiment, the present invention relates to a method of treating actinic keratoses using photodynamic therapy, wherein the affected area of the skin of a patient is illuminated with a light source after application of ALA. The light source may be selected from any physical light-generating device that generates blue, red, or white wavelengths, for example, the light source may be an arc lamp, an incandescent light (glowing filament), a fluorescent source (glowing gas), a laser (coherent light), a red light source, a halogen laser, a blue light source or a light emitting diode (LED).

In a preferred embodiment, the light source is a blue light source. In a more preferred embodiment, the light source is a blue light having a wavelength of approximately 417 nm and is applied at an intensity of 10 mW/cm$^2$ for 1000 seconds to provide a dose of 10 J/cm$^2$. In other embodiments, the intensity may be increased (for example, doubled) to reduce the treatment time. For example, the intensity may be increased to an extent wherein the treatment time becomes about one-half of the original treatment time. In another embodiment the intensity of the light may be decreased (for example, with neutral density filters) so as to increase the treatment time.

In another preferred embodiment, the light source is a red light source. In a more preferred embodiment, the red light source is a red light generated by light emitting diodes (LEDs) at, for example, 635 nm. The red light can provide a dose of, for example, 10 to 75 J/cm$^2$ (such as 37 J/cm$^2$), e.g., within 10 minutes. In other embodiments, the intensity may be increased (for example, doubled) to reduce the treatment time. For example, the intensity may be increased to an extent wherein the treatment time becomes about one-half of the original treatment time. In another embodiment the intensity of the light may be decreased (for example, with neutral density filters) so as to increase the treatment time.

In one embodiment of the invention, the VAS pain score achieved from the method of treating actinic keratoses using photodynamic therapy is less than 1.0. In preferred embodiments, the VAS pain score is selected from a value which is less than 0.9, less than 0.8, less than 0.7 or less than 0.6. In a more preferred embodiment, the VAS pain score is selected from a value which is less than 0.5, less than 0.4, less than 0.3, less than 0.2 or less than 0.1. In the most preferred embodiment, the VAS Pain Score is 0.0.

EXAMPLES

The Examples that follow are illustrative of specific embodiments of the disclosure, and various uses thereof. They are set forth for explanatory purposes only and should not be construed as limiting the scope of the disclosure in any way.

Example 1: Bilaterally Controlled, Randomized Clinical Trial

1. Methods:

Study Design

This prospective, randomized clinical trial was a bilaterally controlled study and used a contralateral split-body design. Subjects were recruited from outpatient clinics of the Dermatology Department, Cleveland Clinic and gave informed consent prior to enrollment.

Study Population

Eligible patients had >6 non-hypertrophic actinic keratoses (AK), with >3 lesions on each side of the face or scalp. Candidates using other treatments for AK were excluded. Patients taking doxycycline or topical retinoids were asked to stop at least 2 weeks before receiving PDT.

Randomization

In this bilateral study, left and right halves of the body were compared. Side A (the test side), receiving the experimental blue light regimen, was chosen via a computer-generated, block randomization scheme to insure an equal left/right distribution. The contralateral side was designated as Side B (the control side).

Interventions

On Day 1, ALA 20% solution (Levulan Kerastick) was applied to the entire face and scalp. Side B was shielded with a dark cloth, and Side A was immediately exposed to blue light (Blu-U, 10 mW/cm2). The light dose for Side A was given per a dose escalation scheme, wherein the first patient cohort received 30 min, the second cohort 45 min, and the third cohort 60 min of blue light. Beginning 60 min after ALA application, Side A was shielded, and Side B was illuminated for 1000 seconds (16 min 40 s). After this light exposure, a soothing emollient (Aquaphor) was applied to the treated areas and the patient was sent home wearing a wide-brim hat and instructions to avoid sunlight for 48 hours.

Outcome Measures

The primary endpoint was therapeutic efficacy (AK lesion clearance), defined as reduction in the number of AK lesions between the baseline and Month 3 visits. At each visit, nonhypertrophic AK lesions (Olsen grade 1 or 2) 13 were identified by a study physician using clinical criteria (scale, erythema, roughness to palpation), and each lesion marked with a black pen. Marked lesions were digitally photographed for a permanent record. From the photographs, AK lesions were counted within site-specific regions (face and scalp; right and left of midline). For balding patients, the location of the original hairline was drawn onto photographs to facilitate accurate counting of lesions on the face versus scalp.

Several secondary endpoints were also measured. For pain assessment, patients were asked every 5 to 10 min during illumination to report their pain on a 0 to 10 visual-analog (VAS) scale. Erythema was recorded photographically at Day 1 and on Day 4 post PDT. A side effect profile was recorded by each patient in a daily home questionnaire to document the presence or absence of eleven different signs and symptoms in the 4 days immediately following PDT (see Table 2).

Statistical Analysis

The primary endpoint was AK lesion reduction. For each patient, the lesion reduction rates on the two sides treated by the test and the control regimens respectively were computed; and then the difference of the two reduction rates was computed. The t-test was used to compare the reduction rate difference against a non-inferiority margin of 15%, i.e., the test regime was considered non-inferior to the control regime if its reduction rate was not 15% lower than the control regime. Subgroup analyses were performed for each test cohort (30 min, 45 min, or 60 min), and the same analyses were applied to the scalp data. The secondary endpoint of post-treatment pain scale was analyzed using a linear mixed-effect model since the VAS scale was assessed up to five times on the side receiving the experimental regime and up to three times on the side receiving the control regime. The model included a random effect to account for the repeated measurements and the paired design. Adverse events (side effects) were summarized as descriptive statistics. Statistical significance was considered with a p-value <0.05. All analyses were performed with R 3.5.1 (cran.r-project.org).

Sample Size Justifications

The study was powered to evaluate the primary endpoint of AK lesion clearance. It was estimated that if the difference of lesion clearance between the two sides is 0% and the SD for the difference is 24%, the sample size of 23 patients has a power of 87% for a non-inferiority margin of 15% when the (one-sided alpha=0.05). The power is 80% if the clearance rate on Side A is even 2% higher than Side B.

2. Results:

Twenty-seven patients were screened between May 2014 and October 2016. Of these, 3 did not meet enrollment criteria and 1 was lost to follow-up (FIG. 1). Amongst the remaining 23 patients, 21 were elderly Caucasian men (mean age, 69.7 years, range 58-88 years) and two were women (ages 50 and 73). Overall, this population had abundant AK lesions, ranging from total counts of 23 to 70 on the face, and 0 to 123 on the scalp. Only 7 patients had no AK on the scalp.

At the outset, the consequences of a long blue light exposure to the face were unknown, so a light-dose escalation scheme was employed to ensure patient safety (FIG. 1).

For the first patient cohort, the duration of blue light received by side A of was limited to 30 min. The side effect profile amongst this group was acceptable, so subsequent cohorts received 45 min (8 patients), or 60 min (8 patients) on Side A. All patients received a dose of 1000 seconds of blue light to Side B. Erythema, an early indicator of PDT response, was typically very mild at the conclusion of treatment, but increased markedly over the next 1-4 days. As illustrated in FIG. 2, spotty erythema (corresponding to inflamed AK lesions) appeared to be approximately equal on Side A and Side B; this was true for the majority of patients.

The primary endpoint, clinical efficacy, was defined as % reduction in AK lesion counts at 3 months. Data in Table 1 show that clinical efficacy was nearly identical on both sides of the face and scalp. This was confirmed statistically (by a test of non-inferiority) for both face and scalp, indicating that test PDT and the control PDT provide essentially identical treatment efficacy. In addition, there was no statistical difference in efficacy between the three test PDT cohorts (30, 45, and 60 min), for either face or scalp (Table 1).

Pain during blue light illumination was a secondary endpoint. When VAS pain scores (reported every 5-10 min by the patients) were averaged, the mean scores were 0.52 (95% CI=[0, 1.09]) on Side A, versus 3.57 (95% CI=[2.97, 4.16]) on Side B. This difference was statistically significantly, with a p-value <0.001. As additional documentation, maximum pain scores are reported in FIG. 3, which further illustrates the vast reduction in pain experienced with test PDT versus the control PDT.

The inflammatory side effects that patients experienced during the first few days following PDT were also examined. Table 2 shows the aggregate results of the daily questionnaire completed by every patient during the first 4 days post-treatment. Post-PDT inflammatory responses developed gradually. Maximum values for burning, itching, redness, stinging, and swelling were observed by day 2 post-PDT (Table 2). At days 3 and 4, those parameters began to decrease and were supplanted by increased crusting and peeling, reflecting the normal course of resolution after PDT. Importantly, no noticeable differences amongst the major inflammatory parameters were observed when comparing Side A and Side B. These results confirm that test PDT with substantially no-pre-illumination gap, is not only much less painful than the control PDT with a longer pre-illumination gap, but also produces an equally good efficacy for the treatment of actinic keratoses lesions.

TABLE 1

| Clinical response (% reduction in AK counts at 3 months) | | | | |
| --- | --- | --- | --- | --- |
| | Side A 1 (Test side) | Side B 2 (Control side) | Difference (A − B) | P-value [3] |
| Face | | | | |
| All patients: | 57.7% | 59.1% | −1.4% [−13.8%, 10.9%] | 0.016 |
| 30 min cohort | 55.4% | 57.1% | −1.7% [−25.1%, 21.7%] | 0.133 |
| 45 min cohort | 59.8% | 58.6% | 1.1% [−20.8%, 23.0%] | 0.074 |
| 60 min cohort | 57.5% | 61.2% | −3.8% [−25.6%, 18.1%] | 0.157 |
| Scalp | | | | |
| All patients: | 43.8% | 41.9% | 1.9% [−6.9%, 10.8%] | <.001 |
| 30 min cohort | 44.8% | 46.0% | −1.2% [−18%, 15.6%] | 0.054 |

TABLE 1-continued

| | Clinical response (% reduction in AK counts at 3 months) | | | |
|---|---|---|---|---|
| | Side A 1 (Test side) | Side B 2 (Control side) | Difference (A − B) | P-value [3] |
| 45 min cohort | 41.2% | 38.2% | 3% [−13.8%, 19.8%] | 0.018 |
| 60 min cohort | 45.2% | 41.5% | 3.7% [−11.7%, 19.0%] | 0.009 |

AK lesion reduction, defined as percent decrease in AK lesion counts observed at 3 months relative to baseline.
Also, note that lesion reduction after test PDT does not differ amongst the three cohorts, either on the face (p = 0.95) nor the scalp (p = 0.91), respectively.
[1] Side A, test PDT with substantially no pre-illumination gap
[2] Side B, control PDT regimen (1 hr. pre-illumination gap after ALA application, followed by blue light illumination for 1000 sec.).
[3] P-value: One-sided p-values from non-inferiority tests, using a margin of 15%.

15

TABLE 2

| | Comparison of inflammatory responses during the first 4 days | | | |
|---|---|---|---|---|
| Symptom [3] | DAY 1 Side A[1], Side B[2] | DAY 2 Side A[1], Side B[2] | DAY 3 Side A[1], Side B[2] | DAY 4 Side A[1], Side B[2] |
| (A) Bleeding | 0, 0 | 17, 0 | 13, 4 | 17, 13 |
| (B) Blisters | 13, 13 | 4, 9 | 17, 13 | 4, 9 |
| (C) Burning | 65, 65 | 52, 52 | 35, 35 | 26, 26 |
| (D) Crusting | 9, 4 | 9, 17 | 30, 26 | 35, 35 |
| (E) Itching | 43, 43 | 74, 74 | 70, 65 | 65, 65 |
| (F) Open sores | 0, 0 | 9, 9 | 9, 9 | 4, 4 |
| (G) Peeling | 4, 0 | 4, 9 | 22, 26 | 48, 52 |
| (H) Redness | 91, 91 | 100, 100 | 91, 87 | 83, 74 |
| (I) Stinging | 65, 65 | 70, 70 | 39, 39 | 35, 35 |
| (J) Swelling | 26, 22 | 26, 26 | 9, 13 | 0, 0 |
| (K) Pain Score [4] Mean: | 3.0, 2.9 | 2.5, 2.4 | 1.6, 1.5 | 1.0, 1.0 |
| SEM: | ±0.64, ±0.62 | ±0.53, ±0.51 | ±0.33, ±0.31 | ±0.22, ±0.21 |

[1]Side A received test PDT with substantially no pre-illumination gap
[2]Side B received control PDT regimen (1 hr. pre-illumination gap after ALA application, followed by blue light illumination for 1000 sec.
[3] Each value in the table is a percentage of patients who reported the particular symptom (A to J).
[4] Average pain score (0-10 visual-analog scale) reported by the 23 patients, on Side A and Side B.

TABLE 3

| | Patient demographics and initial AK lesion counts | | | |
|---|---|---|---|---|
| Patient ID | Sex | Age (Years) | No. of AK on Face | No. of AK on Scalp |
| (1) 30b-18 | F | 73 | 24 | 0 |
| (2) 30b-17 | M | 72 | 50 | 34 |
| (3) 30-04 | M | 87 | 37 | 62 |
| (4) 30-03 | M | 70 | 105 | 0 |
| (5) 30b-16 | M | 71 | 46 | 0 |
| (6) 30-05 | M | 73 | 37 | 20 |
| (7) 30b-29 | M | 88 | 70 | 123 |
| (8) 45b-19 | M | 73 | 55 | 25 |
| (9) 45-06 | M | 58 | 19 | 38 |
| (10) 45b-20 | M | 74 | 39 | 125 |
| (11) 45-10 | M | 61 | 20 | 26 |
| (12) 45-07 | M | 72 | 23 | 0 |

TABLE 3-continued

| | Patient demographics and initial AK lesion counts | | | |
|---|---|---|---|---|
| Patient ID | Sex | Age (Years) | No. of AK on Face | No. of AK on Scalp |
| (13) 45-08 | M | 58 | 28 | 34 |
| (14) 45b-21 | M | 66 | 49 | 97 |
| (15) 45b-23 | M | 69 | 36 | 0 |
| (16) 60-12 | M | 74 | 23 | 20 |
| (17) 60-15 | M | 76 | 20 | 18 |
| (18) 60-14 | M | 69 | 9 | 25 |
| (19) 60-13 | M | 72 | 44 | 0 |
| (20) 60-11 | M | 70 | 20 | 26 |
| (21) 60b-24 | M | 63 | 33 | 56 |
| (22) 60b-25 | M | 66 | 27 | 49 |
| (23) 60b-26 | F | 50 | 53 | 0 |

TABLE 4

Pain scores reported during test vs control PDT illumination
Pain values shown here were reported every 5 to 10 minutes on a 0-to-10 visual-analog scale (VAS). A value of 10 was defined as unbearable pain.

| | SIDE A (test PDT) Time during illumination (min) | | | | | | SIDE B (control PDT) Time during illumination (min) | | | |
|---|---|---|---|---|---|---|---|---|---|---|
| Patient ID | 10 ' | 20 ' | 30 ' | 40 ' | 50 ' | Mean | 5 ' | 10 ' | 15 ' | Mean |
| (1) 30b-18 | 0 | 0 | 0 | — | — | 0.0 | 5 | 5 | 4 | 4.7 |
| (2) 30b-17 | 0 | 0 | 0 | — | — | 0.0 | 2 | 1 | 0 | 1.0 |

TABLE 4-continued

Pain scores reported during test vs control PDT illumination
Pain values shown here were reported every 5 to 10 minutes on a 0-to-10 visual-
analog scale (VAS). A value of 10 was defined as unbearable pain.

| | SIDE A (test PDT) Time during illumination (min) | | | | | | SIDE B (control PDT) Time during illumination (min) | | | |
|---|---|---|---|---|---|---|---|---|---|---|
| Patient ID | 10 ' | 20 ' | 30 ' | 40 ' | 50 ' | Mean | 5 ' | 10 ' | 15 ' | Mean |
| (3) 30-04 | 2 | 2 | 2 | — | — | 2.0 | 10 | 7 | 5 | 7.3 |
| (4) 30-03 | 3 | 5 | 6 | — | — | 4.7 | 10 | 5 | 6 | 7.0 |
| (5) 30b-16 | 0 | 1 | 1 | — | — | 0.7 | 4 | 4 | 4 | 4.0 |
| (6) 30-05 | 1 | 1 | 1 | — | — | 1.0 | 5 | 3 | 1 | 3.0 |
| (7) 30b-29 | 0 | 0 | 0 | — | — | 0.0 | 3 | 3 | 3 | 3.0 |
| (8) 45b-19 | 0 | 0 | 0 | 0 | — | 0.0 | 8 | 3 | 0 | 3.7 |
| (9) 45-06 | 1 | 0 | 0 | 0 | — | 0.3 | 4 | 3 | 2 | 3.0 |
| (10) 45b-20 | 1 | 1 | 1 | 1 | — | 1.0 | 3 | 3 | 2 | 2.7 |
| (11) 45-10 | 0 | 0 | 0 | 0 | — | 0.0 | 2 | 2 | 1 | 1.7 |
| (12) 45-07 | 0 | 0 | 0 | 1 | — | 0.3 | 4 | 4 | 3 | 3.7 |
| (13) 45-08 | 0 | 0 | 0 | 0 | — | 0.0 | 4 | 5 | 4 | 4.3 |
| (14) 45b-21 | 1 | 1 | 0 | 0 | — | 0.5 | 5 | 5 | 5 | 5.0 |
| (15) 45b-23 | 0 | 0 | 0 | 0 | — | 0.0 | 1 | 1 | 2 | 1.3 |
| (16) 60-12 | 0 | 0 | 0 | 0 | 0 | 0.0 | 1 | 1 | 0 | 0.7 |
| (17) 60-15 | 1 | 0 | 1 | 1 | 1 | 0.8 | 8 | 6 | 5 | 6.3 |
| (18) 60-14 | 0 | 0 | 0 | 0 | 1 | 0.2 | 5 | 4 | 4 | 4.3 |
| (19) 60-13 | 0 | 0 | 0 | 0 | 0 | 0.0 | 1 | 1 | 1 | 1.0 |
| (20) 60-11 | 0 | 0 | 0 | 0 | 0 | 0.0 | 4 | 4 | 3 | 3.7 |
| (21) 60b-24 | 0 | 1 | 1 | 1 | 1 | 0.8 | 8 | 7 | 5 | 6.7 |
| (22) 60b-25 | 0 | 0 | 0 | 0 | 0 | 0.0 | 0 | 1 | 0 | 0.3 |
| (23) 60b-26 | 0 | 0 | 0 | 0 | 0 | 0.0 | 2 | 4 | 5 | 3.7 |

Statistical comparison of VAS pain scores between test and control PDT regimens: The mean score on Side A was 0.52 (95% CI = [0, 1.09]), and on Side B was 3.57 (95% CI = [2.97, 4.16]). The two sides were significantly different, with a p-value < 0.001.

3. Discussion:

In this study, there was substantially no pre-illumination gap between ALA application and illumination using a blue light source. The trial had a bilaterally-controlled study design in which each patient served as his/her own control. Results showed that pain was drastically reduced on the side receiving the "test" PDT regimen with substantially no pre-illumination gap. Equally important is the finding that the therapeutic response (lesion clearance) was statistically indistinguishable from the side receiving "test" PDT with 1 hour pre-illumination gap.

The ability to perform PDT painlessly, while achieving good lesion clearance, should help to optimize therapeutic response in several ways. First, a single PDT treatment is seldom sufficient for complete AK clearance; this is why PDT clinical trials to maximize efficacy typically employ two PDT treatments spaced 8 weeks apart (Piacquadio D J et al. Arch Dermatol 2004; 140:41-6; Pariser D M et al. Dermatol Surg 2016; 42:296-304), and why European PDT protocols generally recommend two treatments (Braathen L R et al. J Am Acad Dermatol 2007; 56:125-43). The results with respect to significantly high efficacy and no pain on one side of the face/scalp that received test PDT will help to convince patients to undergo multiple PDT sessions, since pain should no longer be an issue. Also, the test PDT regimen significantly reduces office wait times. Instead of several hours for a pre-illumination gap, a PDT with substantially no pre-illumination gap before the blue light illumination may take only 45-60 minutes, even allowing for more careful explanation of aftercare instructions to the patient.

The present invention has surprisingly found a method to significantly reduce the pain experienced during photodynamic therapy. While the above example shows a reduction in pain score in comparison to merely 1 hour pre-illumination gap as a comparator arm; in clinical practice of PDT of actinic keratoses, wherein the FDA approved pre-illumination gap is 14-16 hours, the reduction in pain score will be even more significant and is expected to result into a painless or nearly painless photodynamic therapy of actinic keratosis.

The invention claimed is:

1. A method of reducing pain during a photodynamic therapy of actinic keratoses comprising:
   (a) applying a pharmaceutical composition comprising 20% w/v solution of 5-aminolevulinic acid on an affected area of skin of a patient;
   (b) illuminating the affected area with a blue light source applied at an intensity of 10 mW/cm$^2$ with a pre-illumination gap of no more than 10 minutes; and
   (c) maintaining the illumination for at least 45 minutes; wherein the method does not include a pre-treatment preparation.

2. The method according to claim 1, wherein the blue light source delivers a light having a wavelength of 417 nm±5 nm.

3. The method according to claim 1, wherein the actinic keratoses is of face and/or scalp.

4. The method according to claim 1, wherein the illumination of step (c) is carried out for at least 60 minutes.

5. The method according to claim 1, wherein the method results in a significantly reduced VAS pain score as compared to a photodynamic therapy with a pre-illumination gap of at least 60 minutes.

6. The method according to claim 5, wherein the resulting VAS pain score is less than 1.0.

7. The method according to claim 5, wherein the resulting VAS pain score is 0.5+0.5.

8. The method according to claim 5, wherein the resulting VAS pain score is 0.0.

9. A method of treating actinic keratoses comprising:
   (a) applying a pharmaceutical composition comprising 20% w/v solution of 5-aminolevulinic acid on an affected area of skin of a patient;

(b) illuminating the affected area with a blue light source applied at an intensity of 10 mW/cm$^2$ with a pre-illumination gap of no more than 10 minutes; and (c) maintaining the illumination for at least 45 minutes; wherein the method does not include a pre-treatment preparation.

10. The method according to claim 9, wherein the blue light source delivers a light having a wavelength of 417 nm±5 nm.

11. The method according to claim 9, wherein the illumination of step (c) is carried out for at least 60 minutes.

12. The method according to claim 9, wherein the method results in a significantly reduced VAS pain score as compared to a photodynamic therapy with a pre-illumination gap of at least 60 minutes.

13. The method according to claim 12, wherein the resulting VAS pain score is less than 1.0.

14. The method according to claim 12, wherein the resulting VAS pain score is 0.5±0.5.

15. The method according to claim 12, wherein the resulting VAS pain score is 0.0.

* * * * *